(12) United States Patent
Huertas Carrillo et al.

(10) Patent No.: US 11,087,497 B2
(45) Date of Patent: Aug. 10, 2021

(54) CHEMICAL DETECTION SYSTEM FOR WATER SOURCE

(71) Applicant: International Business Machines Corporation, Armonk, NY (US)

(72) Inventors: Gloriana Huertas Carrillo, San Jose (CR); Luis Carlos Cruz Huertas, San Pedro (CR); Lee N. Helgeson, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 98 days.

(21) Appl. No.: 16/572,668

(22) Filed: Sep. 17, 2019

(65) Prior Publication Data
US 2021/0082150 A1   Mar. 18, 2021

(51) Int. Cl.
*G06T 7/90*    (2017.01)
*G06N 20/00*   (2019.01)
*G06N 5/04*    (2006.01)
*G06K 9/46*    (2006.01)
*G06K 9/62*    (2006.01)
(Continued)

(52) U.S. Cl.
CPC .............. *G06T 7/90* (2017.01); *G01N 33/18* (2013.01); *G06K 9/4652* (2013.01); *G06K 9/627* (2013.01); *G06K 9/6223* (2013.01); *G06N 5/04* (2013.01); *G06N 20/00* (2019.01); *G08B 21/02* (2013.01); *G06T 2207/10016* (2013.01);
(Continued)

(58) Field of Classification Search
CPC ............ G06T 7/90; G06T 2207/10016; G06T 2207/10024; G06T 2207/20081; G06T 2207/30181; G06N 20/00; G06N 5/04; G01N 33/18; G06K 9/4652; G06K 9/6223; G06K 9/627; G08B 21/02
USPC ........................................................ 382/100
See application file for complete search history.

(56) References Cited

U.S. PATENT DOCUMENTS 4,125,376 A   11/1978  Razulis
5,116,759 A    5/1992  Klainer
(Continued)

FOREIGN PATENT DOCUMENTS

CN      101929956 A    12/2010
CN      203011912 U     6/2013
(Continued)

OTHER PUBLICATIONS

Hsieh et al., "Spectral imaging of chemical reactions using a computer display and a digital camera", ResearchGate, 4(59).31094-31100 · Jul. 2014, <https://www.researchgate.net/publication/264942191_Spectral_imaging_of_chemical_reactions_using_a_computer_display_and_a_digital_camera>, 8 pages.
Pavan Kumaar et el., "Air and Water Quality Monitoring Through IOT by Using Aquatic Surface Drone", International Journal of Pure and Applied Mathematics, vol. 118 No. 22 2018, 51-55 ISSN: 1314-3395, <https://acadpubl.eu/hub/2018-118-22/articles/22a/7.pdf>, 6 pages.
(Continued)

*Primary Examiner* — Michael R Neff
(74) *Attorney, Agent, or Firm* — Stephanie L. Carusillo

(57) ABSTRACT

In an approach for chemical detection for a water source, a processor receives, from a network device of a plurality of network devices, data, wherein the data includes at least one of image data, video data, chemical sensor data, and biosensor data. A processor updates a predictive model with the data. A processor receives a table of possible chemical compositions from the predictive model. A processor determines to send an alert based on the table of possible chemical compositions. A processor sends the alert to a user device.

17 Claims, 3 Drawing Sheets

(51) Int. Cl.
*G08B 21/02* (2006.01)
*G01N 33/18* (2006.01)

(52) U.S. Cl.
CPC .............. *G06T 2207/10024* (2013.01); *G06T 2207/20081* (2013.01); *G06T 2207/30181* (2013.01)

(56) References Cited

U.S. PATENT DOCUMENTS

| | | | |
|---|---|---|---|
| 5,624,537 A | 4/1997 | Turner | |
| 6,574,363 B1 | 6/2003 | Classen | |
| 6,753,816 B1 | 6/2004 | Apostolos | |
| 7,391,333 B2 | 6/2008 | Madden | |
| 7,591,979 B2 | 9/2009 | Hill | |
| 7,866,204 B2 | 1/2011 | Yang | |
| 2003/0236649 A1* | 12/2003 | Kodukula | C02F 1/008 702/188 |
| 2006/0188398 A1 | 8/2006 | Yano | |
| 2013/0304395 A1* | 11/2013 | Naidu | G06N 3/126 702/25 |
| 2016/0340206 A1 | 11/2016 | Antos | |
| 2017/0276660 A1 | 9/2017 | Ba | |

FOREIGN PATENT DOCUMENTS

| | | |
|---|---|---|
| CN | 103808907 A | 5/2014 |
| KR | 101362820 B1 | 2/2014 |

OTHER PUBLICATIONS

Reddy, D. Sreenivasulu, "Implementation of Smart Sensor Interface for Water Quality Monitoring in IOT (Internet of Things) Environment", International Journal of Innovative Research in Computer and Communication Engineering, vol. 1, Issue 6, Aug. 2013, 8 pages.

Robertson, Bill, "Why Does a Color Change Indicate a Chemical Change?", NSTA WebNews Digest Science and Children : Science 101, Jan. 20, 2006, <//www.nsta.org/publications/news/story.aspx?id=51520>, 3 pages.

Salzer et al., "Infrared and Raman Spectroscopic Imaging", <https://books.google.com.vn/books?id=HGdEBAAAQBAJ&pg=PA67&lpg=PA67&dq=chemical+composition+through+images&source=bl&ots=vT57qatXEY&sig =nwTJ1sc8sgWXnlc-et85qyQO5D0&hl=en&sa=X&ved=0ahUKEwjepqX_vKrbAhUKfLwKHQrdCzsQ6AEIYTAL#v=onepage&q=chemical%20composition%20through%20images&f=false>, John Wiley & sons. Copyright Jan. 2014, 71 pages.

Seeley et al., "Early Warning Chemical Sensing", vol. 17, No. 1, 2007 Lincoln Laboratory Journal, <https://www.ll.mit.edu/publications/journal/pdf/vol17_no1/17_1_4Seeley.pdf>, 15 pages.

Shkurin, Aleksei, "Water Quality Analysis Using Machine Learning Algorithms", Bachelor's Thesis in Environmental Engineering, <https://www.theseus.fi/bitstream/handle/10024/106320/Shkurin_Aleksei.pdf?sequence=1>, Dec. 2015, 54 pages.

Singh et al., "Review on Data Mining Techniques for Prediction of Water Quality", International Journal of Advanced Research in Computer Science, vol. 8, No. 5, May-Jun. 2017, 6 pages.

\* cited by examiner

CHEMICAL DETECTION SYSTEM FOR WATER SOURCE

BACKGROUND

The present invention relates generally to the field of chemical detection, and more particularly to chemical detection for a water source.

The water quality of a water source can be assessed by measuring chemical attributes of the water source. Chemical attributes of water can affect aesthetic qualities such as how water looks, smells, and tastes. Chemical attributes of water can also affect its toxicity and whether or not it is safe to use. Since the chemical quality of water is important to the health of humans as well as the plants and animals that live in and around the water source, the assessment of the chemical attributes of water is necessary. Assessment of water quality by its chemistry includes measures of many elements and molecules dissolved or suspended in the water. Chemical measures can be used to directly detect pollutants and/or imbalances within an ecosystem.

Commonly measured chemical parameters include pH, alkalinity, hardness, nitrates, nitrites and ammonia, ortho- and total phosphates, and dissolved oxygen and biochemical oxygen demand. In addition, some "chemical" measurements actually indicate the physical presence of pollutants in water. These include measurements such as conductivity and density.

Although water quality is usually sampled and analyzed at laboratories, there has been increasing public interest in the quality of drinking water provided by municipal systems. Many water utilities have developed systems to collect real-time data about source water quality. A variety of sensors and remote monitoring systems have been deployed for measuring water pH, turbidity, dissolved oxygen and other parameters. Some remote sensing systems have also been developed for monitoring ambient water quality in riverine, estuarine and coastal water bodies.

SUMMARY

Aspects of an embodiment of the present invention disclose a method, computer program product, and computer system for chemical detection for a water source. A processor receives, from a network device of a plurality of network devices, data, wherein the data includes at least one of image data, video data, chemical sensor data, and biosensor data. A processor updates a predictive model with the data. A processor receives a table of possible chemical compositions from the predictive model. A processor determines to send an alert based on the table of possible chemical compositions. A processor sends the alert to a user device.

DETAILED DESCRIPTION

Embodiments of the present invention recognize that the chemical quality of water is important to the health of humans as well as the plants and animals that live in and around a water source. Currently, sensors are used to detect whether there are chemicals in a water source, but the collection of samples and the analysis process can take hours to weeks before a determination is made. Embodiments of the present invention recognize the need for a chemical detection system for a static or dynamic water source that is faster and more efficient.

Embodiments of the present invention provide a cohesive detection system that utilizes visual detection, biosensors, and chemical sensors interconnected to an Internet of Things (IoT) network in order to detect and predict potential pollutants in either a static or dynamic water source. Embodiments of the present invention provide a detection system for historical data capture analysis mapping and processing of real-time water color and water pollution analytics. The detection system harnesses machine-learning and an IoT network to provide new insights and improve identification of water pollutants, particularly nuclear and chemical pollutants. The detection system combines video, pictures, and IoT chemical and bio-sensors to provide delineation of a pollution network using machine-learning and clustering methods to uncover potential roles of chemicals in the water contamination levels. Overall, embodiments of the present invention provide a detection system that maps out a water source to better predict potential pollutants in the water and identifies hierarchical pollutant risk using clustering methods.

Embodiments of the present invention detects, but are not limited to, the following chemical properties and/or dissolved ions in the water source using IoT devices: pH, dissolved oxygen (DO), oxidation-reduction potential (ORP), conductivity (salinity), turbidity, temperature, Fluoride ($F^-$), Calcium ($Ca^{2+}$), Nitrate ($NO_3^-$), Chloride ($Cl^-$), Iodide ($I^-$), Cupric ($Cu^{2+}$), Bromide ($Br^-$), Silver ($Ag^+$), Fluoroborate ($BF_4^-$), Ammonia ($NH_4$), Lithium ($Li^+$), Magnesium ($Mg^{2+}$), Nitrite ($NO_2^-$), Perchlorate ($ClO_4$), Potassium ($K^+$), Arsenic ($As^{3+}$), and Sodium ($Na^+$).

Implementation of embodiments of the invention my take a variety of forms, and exemplary embodiments are discussed subsequently with reference to the Figures.

Figure 1:
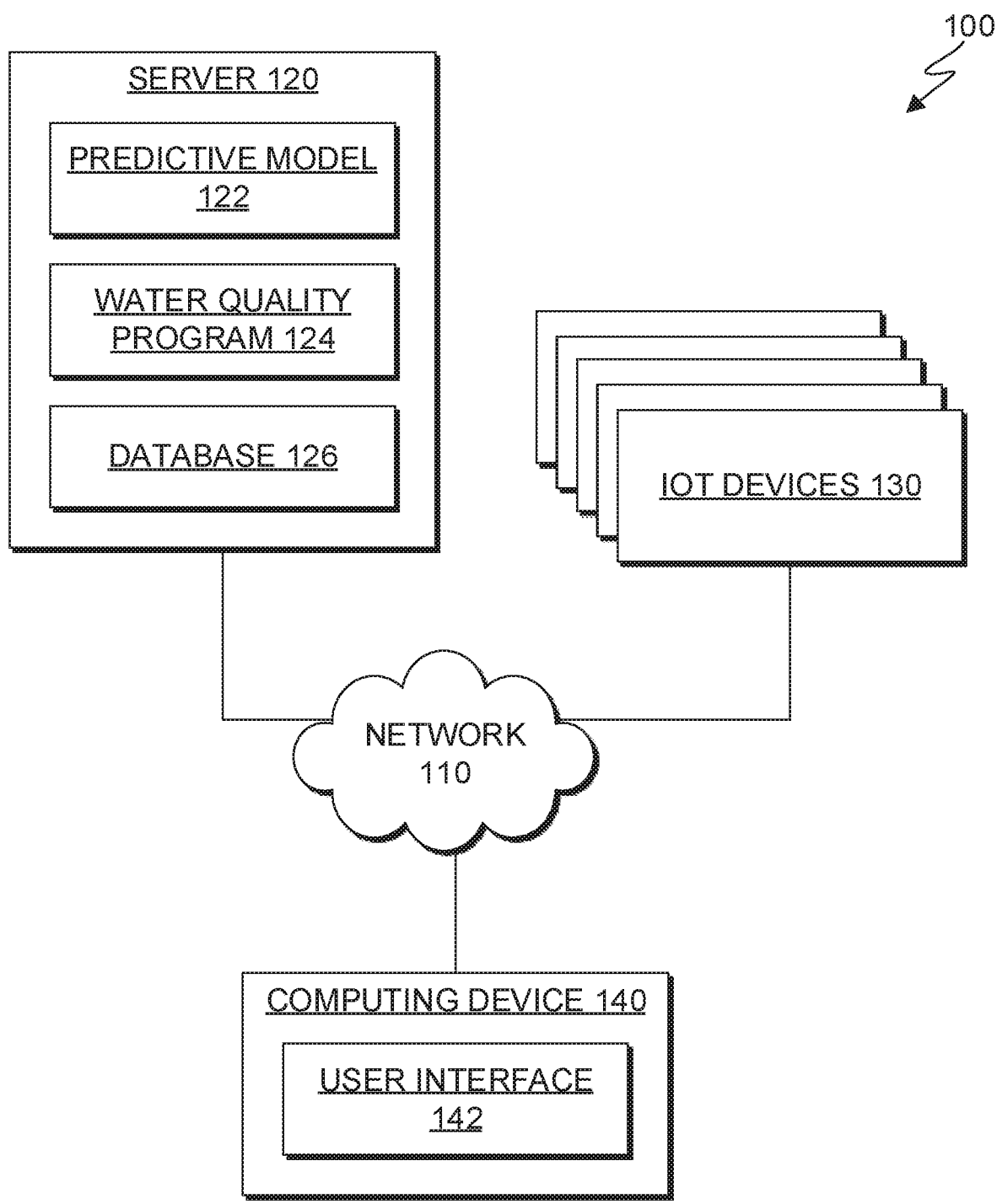
FIG. 1 depicts a block diagram of a distributed data processing environment, in accordance with an embodiment of the present invention.

FIG. 1 is a functional block diagram illustrating distributed data processing environment 100, in accordance with one embodiment of the present invention. The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

In the depicted embodiment, distributed data processing environment 100 includes server 120, IoT devices 130, and user computing device 140 interconnected over network 110. Network 110 can be, for example, a telecommunications network, a local area network (LAN), a wide area network (WAN), such as the Internet, or a combination of the three, and can include wired, wireless, or fiber optic connections. Network 110 can include one or more wired and/or wireless networks capable of receiving and transmitting data, voice, and/or video signals, including multimedia signals that include voice, data, and video information. In general, network 110 can be any combination of connections and protocols that will support communications between server 120, IoT devices 130, user computing device 140, and other computing devices (not shown) within distributed data processing environment 100. Distributed data processing environment 100 may include additional servers, computers, IoT devices, or other devices not shown.

Server 120 operates to run predictive model 122, water quality program 124, and store and/or send data using database 126. In an embodiment, server 120 is an artificial intelligence (AI) computing system that uses IoT data and machine learning to map out the water system/source and to train and update predictive model 122 used by water quality program 124 to determine whether the water system/source is contaminated based on data received by IoT devices 130. In an embodiment, server 120 can send data from database 126 to IoT devices 130, user computing device 140, and/or another computing device (not shown). In an embodiment, server 120 can receive data to store in database 126 from IoT devices 130, user computing device 140, and/or another computing device (not shown). In some embodiments, server 120 may be a management server, a web server, or any other electronic device or computing system capable of receiving and sending data. In some embodiments, server 120 may be a laptop computer, tablet computer, netbook computer, personal computer (PC), a desktop computer, a smart phone, or any programmable electronic device capable of communicating with IoT devices 130 and user computing device 140 via network 110. In other embodiments, server 120 represents a server computing system utilizing multiple computers as a server system, such as in a cloud computing environment. Server 120 may include components as described in further detail in FIG. 3.

Predictive model 122 operates to correlate input data from IoT devices, e.g., IoT devices 130, with chemical compositions through k-mean cluster color mapping combined with machine learning classifier methods. Predictive model 122 is trained on identifying colors from unstructured video and/or image data using k-means clustering. Predictive model 122 is also trained on matching color data with chemical compositions.

In an embodiment, predictive model 122 receives structured data of at least one identified chemical composition from a biosensor and/or chemical sensor of IoT devices 130. In an embodiment, predictive model 122 receives unstructured video and/or image data from IoT devices 130 and analyzes the video and/or image data to identify at least one color of the water, and, more specifically, at least one color pallet code. With each input of unstructured and structured data, predictive model 122 updates the k-means clustering and machine learning classifier to improve with each iteration.

Predictive model 122 uses k-means clustering of colors, and, more specifically, color pallet codes to identify at least one color of the water and at least one specific color pallet code from the video and/or image data. In an embodiment, predictive model 122 matches the at least one color pallet code with at least one chemical composition using machine learning classifier methods. In an embodiment, predictive model 122 determines a weight of the color through a weight function and applies a logistic regression for the estimation of the weighted score for each chemical composition based on a distribution of the water coloring data received by predictive model 122, which is updated for each occurrence of data received by water quality program 124. The weight is a result of the goodness of fit test for the distribution of errors from all the IoT data received by predictive model 122. In an embodiment, predictive model 122 calculates a percentage based on the weight corresponding to the possibility that each chemical composition is in the water source. In an embodiment, predictive model 122 outputs a table of the possible chemical compositions with the percentages.

Water quality program 124 operates as a program for monitoring water quality of a water source and outputting an alert when the water source is determined to be possibly contaminated. In an embodiment, water quality program 124 receives data from IoT devices 130. In an embodiment, water quality program 124 updates a predictive model with the data. In an embodiment, water quality program 124 receives a table of possible chemical compositions output by the predictive model. In an embodiment, water quality program 124 outputs an alert. In the depicted embodiment, water quality program 124 resides on server 120. In other embodiments, water quality program 124 may reside on user computing device 140, or another computing device (not shown), provided that water quality program 124 has access to network 110.

Database 126 operates as a repository for unstructured and structured data received from IoT devices 130, k-means clustering data, and predictive model data. A database is an organized collection of data. Database 126 can be implemented with any type of storage device capable of storing data and configuration files that can be accessed and utilized by server 120, such as a database server, a hard disk drive, or a flash memory. Unstructured data sent by IoT devices 130 includes, but is not limited to, image data, video data, and any other type of sensor data that may be unstructured data. Structured data sent by IoT devices 130 includes, but is not limited to, biosensor data, chemical sensor data, and any other type of sensor data that may be structured data. In an embodiment, the unstructured data and structured data received by database 126 can be stored separately within database 126. In other embodiments, the unstructured data and structured data may be stored in separate databases, i.e., database 126 and another database (not shown).

In an embodiment, database 126 is accessed by predictive model 122, water quality program 124, server 120, IoT devices 130, and/or user computing device 140 to store the data sent by IoT devices 130, the k-means clustering data, and/or the predictive model data. In another embodiment, database 126 is accessed by predictive model 122, water quality program 124, server 120, IoT devices 130, and/or user computing device 140 to access the data sent by IoT devices 130, the k-means clustering data, and/or the predictive model data. In the depicted embodiment, database 126 resides on server 120. In another embodiment, database 126 may reside elsewhere within distributed data processing environment 100 provided database 126 has access to network 110.

IoT devices 130 operate as physical devices and/or everyday objects that are embedded with electronics, Internet connectivity, and other forms of hardware (i.e., sensors). In general, IoT devices can communicate and interact with other IoT devices over the Internet while being remotely monitored and controlled. In the depicted embodiment, IoT devices 130 are monitored and controlled by water quality program 124 on server 120 and an owner and/or authorized user through user interface 142 on computing device 140. Types of IoT devices include, but are not limited to, chemical sensors, bio-sensors, smart cameras, smart surveillance cameras, etc. Data collected by IoT devices 130 includes, but is not limited to, picture data, video data, biosensor data, chemical sensor data, and any other type of sensor data.

User computing device 140 operates to run user interface 142 for interacting with an owner and/or authorized user of water quality program 124. In an embodiment, user computing device 140 can send and/or receive data from database 126 and/or water quality program 124 on server 120. In some embodiments, user computing device 140 may be a laptop computer, tablet computer, netbook computer, personal computer (PC), a desktop computer, a smart phone, or any programmable electronic device capable of communicating with server 120 via network 110. In some embodiments, user computing device 140 may be a management server, a web server, or any other electronic device or computing system capable of receiving and sending data. User computing device 140 may include components as described in further detail in FIG. 3.

User interface 142 operates as a local user interface on user computing device 140 of water quality program 124. In an embodiment, user interface 142 is a local mobile application user interface of water quality program 124. In an embodiment, user interface 142 enables an owner and/or authorized user of water quality program 124 to set a threshold value for which a possible chemical contaminant percentage must exceed for an alert to need to be sent. In an embodiment, user interface 142 enables an owner and/or authorized user of water quality program 124 to view an alert that the water source is contaminated. In an embodiment, user interface 142 enables an owner and/or authorized user of water quality program 124 to view an alert and send out the alert to other computing devices (not shown). In an embodiment, user interface 142 enables an owner and/or authorized user of water quality program 124 to generate and send out an alert to necessary parties' computing devices to stop using the water source. In an embodiment, user interface 142 enables an owner and/or authorized user of water quality program 124 to generate and send out an alert to technicians to request manual testing.

Figure 2:
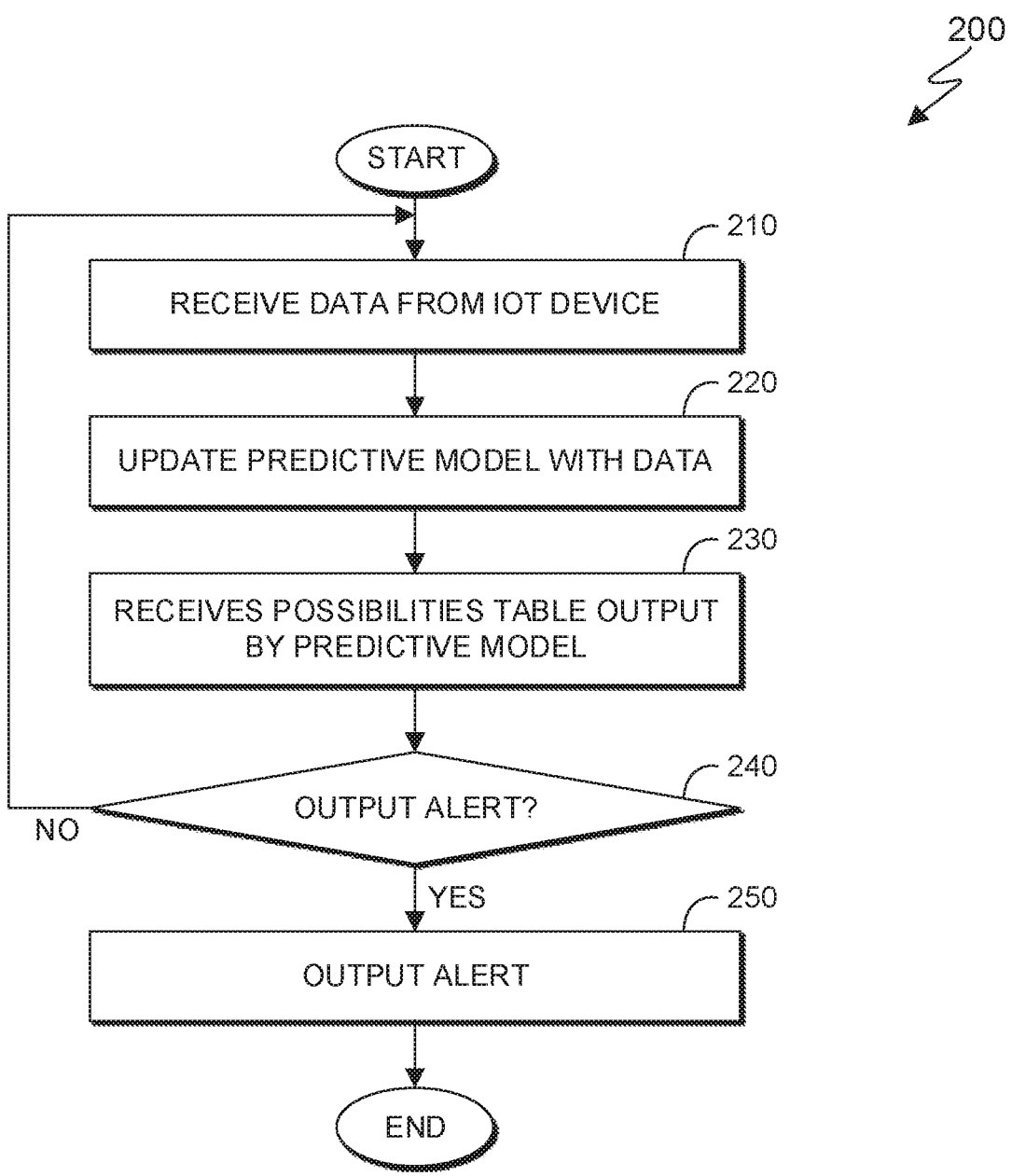
FIG. 2 depicts a flow chart of the steps of a water quality program, in accordance with an embodiment of the present invention.

FIG. 2 depicts a flowchart 200 of the steps of water quality program 124, in accordance with an embodiment of the present invention. In an embodiment, water quality program 124 receives data from an IoT device, updates a predictive model with the data, receives a table of possible chemical compositions output by the predictive model, and outputs an alert. It should be appreciated that the process depicted in FIG. 2 illustrates one possible iteration of the process flow in which water quality program 124 determines the water source is contaminated. In other possible iterations of the process flow (not shown), water quality program 124 could determine the water source is not contaminated based on the data received.

In step 210, water quality program 124 receives data from an IoT device. In an embodiment, water quality program 124 receives unstructured and/or structured data from an IoT device, such as IoT devices 130, in an IoT network, such as IoT network 110. In an embodiment, water quality program 124 receives picture data, video data, biosensor data, chemical sensor data, and/or any other type of sensor data from at least one IoT device, e.g., at least one of IoT devices 130.

In step 220, water quality program 124 updates a predictive model with the data. In an embodiment, water quality program 124 updates the predictive model, e.g., predictive model 122, using the unstructured and/or structured data received. In an embodiment, predictive model 122 analyzes the unstructured and/or structured data. Predictive model 122 uses k-means clustering of colors, and, more specifically, color pallet codes to identify at least one color of the water and at least one specific color pallet code from the video and/or image data. In an embodiment, predictive model 122 matches the at least one color pallet code with at least one chemical composition using machine learning classifier methods.

In an embodiment, predictive model 122 determines a weight of the color through a weight function and applies a logistic regression for the estimation of the weighted score for each chemical composition based on a distribution of the water coloring data. The weight is a result of the goodness of fit test for the distribution of errors from all the IoT data received by predictive model 122. In an embodiment, predictive model 122 calculates a percentage based on the weight corresponding to the possibility that each chemical composition is in the water source. In an embodiment, predictive model 122 outputs a table of the possible chemical compositions with the percentages.

In step 230, water quality program 124 receives the table of possible chemical compositions output by the predictive model. In an embodiment, water quality program 124 receives the table of possible chemical compositions output by predictive model 122. For example, water quality program 124 receives a table of possible chemical compositions output by predictive model 122 with 75% $H_2O+As$, 12.5% $H_2O+NH3$, 12.5% $H2O+NO_3$.

In decision 240, water quality program 124 determines whether to output an alert based on the table of possible chemical compositions. In an embodiment, water quality program 124 reviews the table of possible chemical compositions. In an embodiment, water quality program 124 reviews the percentages in the table and determines whether any of the percentages are above a threshold. In an embodiment, water quality program 124 compares the percentages to a threshold set by the owner and/or authorized user of user computing device 140 through user interface 142. In an embodiment, responsive to a possible chemical composition percentage being above the threshold, water quality program 124 determines to output an alert.

In another embodiment, responsive to a possible chemical composition percentage being above the threshold, water quality program 124 determines whether the chemical composition is on a list of chemical contaminants that have been designated to be harmful to water systems, i.e., environmental organization list, federal governmental list, state governmental list, or a local government list. In an embodiment, responsive to a possible chemical composition percentage being above the threshold and on a water chemical contaminant list, water quality program 124 determines to output an alert.

If water quality program 124 determines to output an alert (decision 240, YES branch), then water quality program 124 proceeds to step 250. If water quality program 124 determines not to output an alert (decision 240, NO branch), then water quality program 124 waits to receive additional data from an IoT device.

In step 250, water quality program 124 outputs an alert. In an embodiment, water quality program 124 outputs an alert to user computing device 140. In an embodiment, water quality program 124 outputs an alert with the table of possible chemical compositions in the water source to user computing device 140. In an embodiment, water quality program 124 outputs an alert with the table of possible chemical compositions in which the possible chemical compositions that exceed the threshold are highlighted and/or delineated in some way. In another embodiment, water quality program 124 outputs an alert with the table of possible chemical compositions in which the possible chemical compositions that are on a governmental water contaminant list are highlighted and/or delineated in some way. In another embodiment, water quality program 124 outputs an alert with the table of possible chemical compositions in which the possible chemical compositions that exceed the threshold and are on a governmental water contaminant list are highlighted and/or delineated in some way.

Figure 3:
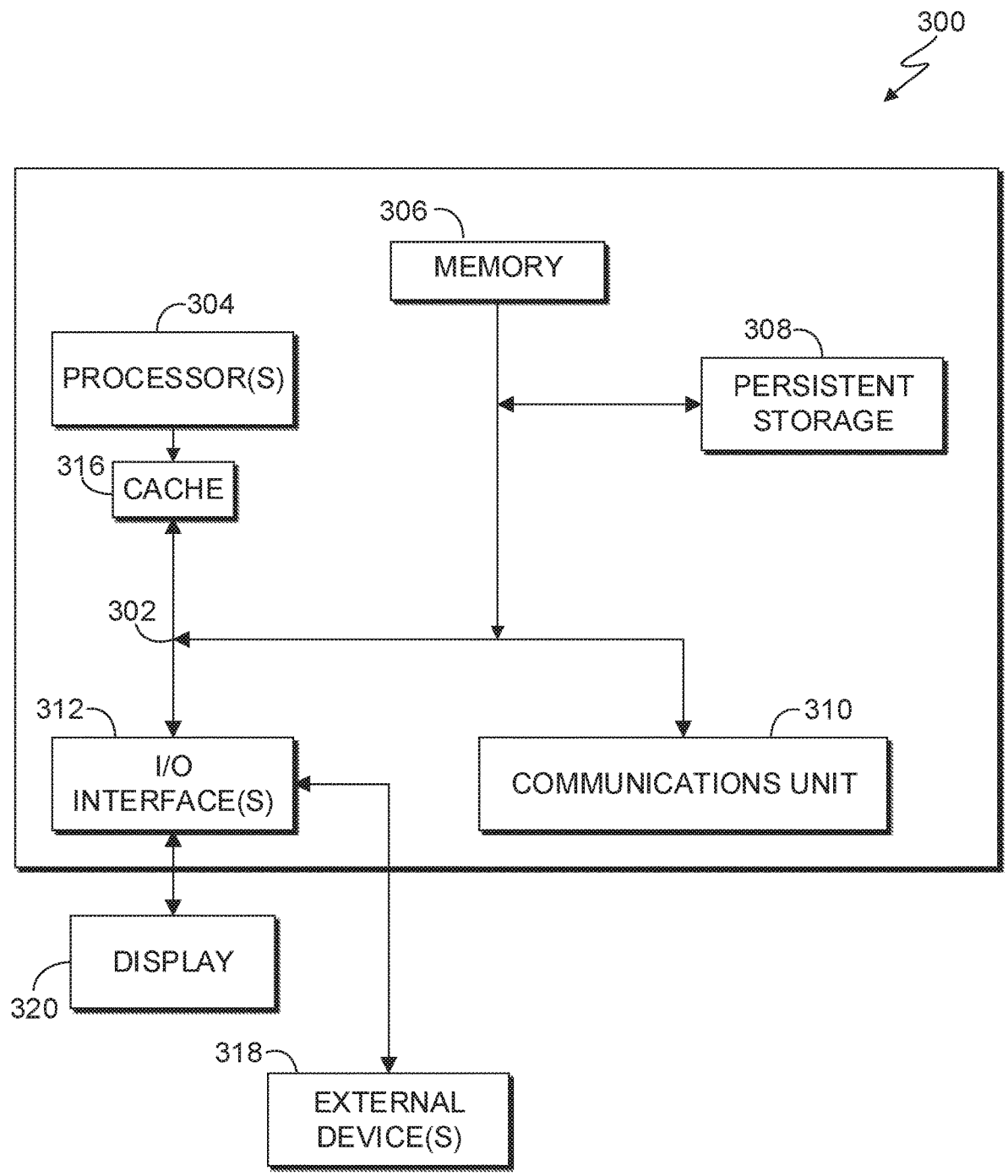
FIG. 3 depicts a block diagram of a computing device of the distributed data processing environment, in accordance with an embodiment of the present invention.

FIG. 3 depicts a block diagram of computer 300 suitable for server 120 and user computing device 140, in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computer 300 includes communications fabric 302, which provides communications between cache 316, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses or a crossbar switch.

Memory 306 and persistent storage 308 are computer readable storage media. In this embodiment, memory 306 includes random access memory (RAM). In general, memory 306 can include any suitable volatile or non-volatile computer readable storage media. Cache 316 is a fast memory that enhances the performance of computer processor(s) 304 by holding recently accessed data, and data near accessed data, from memory 306.

Water quality program 124 may be stored in persistent storage 308 and in memory 306 for execution and/or access by one or more of the respective computer processors 304 via cache 316. In an embodiment, persistent storage 308 includes a magnetic hard disk drive. Alternatively, or in addition to a magnetic hard disk drive, persistent storage 308 can include a solid-state hard drive, a semiconductor storage device, read-only memory (ROM), erasable programmable read-only memory (EPROM), flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 includes one or more network interface cards. Communications unit 310 may provide communications through the use of either or both physical and wireless communications links. Programs, such as water quality program 124, may be downloaded to persistent storage 308 through communications unit 310.

I/O interface(s) 312 allows for input and output of data with other devices that may be connected to server 120, user computing device 140, and IoT devices 130. For example, I/O interface 312 may provide a connection to external devices 318 such as a keyboard, keypad, a touch screen, and/or some other suitable input device. External devices 318 can also include portable computer readable storage media such as, for example, thumb drives, portable optical or magnetic disks, and memory cards. Software and data used to practice embodiments of the present invention can be stored on such portable computer readable storage media and can be loaded onto persistent storage 3308 via I/O interface(s) 312. I/O interface(s) 312 also connect to a display 320.

Display 320 provides a mechanism to display data to a user and may be, for example, a computer monitor.

Water quality program 124 described herein is identified based upon the application for which it is implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for chemical detection for a water source, the computer-implemented method comprising:
    receiving, by one or more processors, from a network device of a plurality of network devices, data, wherein the data includes at least one of image data, video data, chemical sensor data, and biosensor data;
    updating, by one or more processors, a predictive model with the data;
    receiving, by one or more processors, a table of possible chemical compositions from the predictive model;
    determining, by one or more processors, to send an alert based on the table of possible chemical compositions; and
    sending, by one or more processors, the alert to a user device, wherein the alert comprises the table of possible chemical compositions.

2. The computer-implemented method of claim 1, wherein updating the predictive model with the data comprises:
    analyzing, by one or more processors, the data using the predictive model;
    identifying, by one or more processors, at least one color using k-means clustering; and
    matching, by one or more processors, the at least one color to at least one chemical composition using a machine learning classifier of the predictive model.

3. The computer-implemented method of claim 1, wherein determining to send the alert based on the table of possible chemical compositions comprises:
    determining, by one or more processors, whether a weight percentage associated with a chemical composition in the table of possible chemical compositions is above a threshold.

4. The computer-implemented method of claim 1, wherein determining to send the alert based on the table of possible chemical compositions comprises:
    determining, by one or more processors, whether at least one chemical composition in the table of possible chemical compositions are listed on a water chemical contaminant list.

5. The computer-implemented method of claim 1, wherein each chemical composition in the table of possible chemical compositions is weighted based on a distribution of water coloring data.

6. The computer-implemented method of claim 1, wherein the data is unstructured picture or video data.

7. A computer program product for chemical detection for a water source, the computer program product comprising:
one or more computer readable storage media and program instructions stored on the one or more computer readable storage media, the program instructions comprising:
program instructions to receive from a network device of a plurality of network devices, data, wherein the data includes at least one of image data, video data, chemical sensor data, and biosensor data;
program instructions to update a predictive model with the data;
program instructions to receive a table of possible chemical compositions from the predictive model;
program instructions to determine to send an alert based on the table of possible chemical compositions; and
program instructions to send an alert to a user device, wherein the alert comprises the table of possible chemical compositions.

8. The computer program product of claim 7, wherein the program instructions to update the predictive model with the data comprise:
program instructions to analyze the data using the predictive model;
program instructions to identify at least one color using k-means clustering; and
program instructions to match the at least one color to at least one chemical composition using a machine learning classifier.

9. The computer program product of claim 7, wherein the program instructions to determine to send the alert based on the table of possible chemical compositions comprise:
program instructions to determine whether a weight percentage associated with a chemical composition in the table of possible chemical compositions is above a threshold.

10. The computer program product of claim 7, wherein the program instructions to determine to send the alert based on the table of possible chemical compositions comprise:
program instructions to determine whether at least one chemical composition in the table of possible chemical compositions are listed on a water chemical contaminant list.

11. The computer program product of claim 7, wherein each chemical composition in the table of possible chemical compositions is weighted based on a distribution of water coloring data.

12. The computer program product of claim 7, wherein the data is unstructured picture or video data.

13. A computer system for chemical detection for a water source, the computer system comprising:
one or more computer processors;
one or more computer readable storage media;
program instructions stored on the computer readable storage media for execution by at least one of the one or more processors, the program instructions comprising:
program instructions to receive from a network device of a plurality of network devices, data, wherein the data includes at least one of image data, video data, chemical sensor data, and biosensor data;
program instructions to update a predictive model with the data;
program instructions to receive a table of possible chemical compositions from the predictive model;
program instructions to determine to send an alert based on the table of possible chemical compositions; and
program instructions to send an alert to a user device, wherein the alert comprises the table of possible chemical compositions.

14. The computer system of claim 13, wherein the program instructions to update the predictive model with the data comprise:
program instructions to analyze the data using the predictive model;
program instructions to identify at least one color using k-means clustering; and
program instructions to match the at least one color to at least one chemical composition using a machine learning classifier.

15. The computer system of claim 13, wherein the program instructions to determine to send the alert based on the table of possible chemical compositions comprise:
program instructions to determine whether a weight percentage associated with a chemical composition in the table of possible chemical compositions is above a threshold.

16. The computer system of claim 13, wherein the program instructions to determine to send the alert based on the table of possible chemical compositions comprise:
program instructions to determine whether at least one chemical composition in the table of possible chemical compositions are listed on a water chemical contaminant list.

17. The computer system of claim 15, wherein each chemical composition in the table of possible chemical compositions is weighted based on a distribution of water coloring data.

* * * * *